US008076358B2

(12) United States Patent  
Baxter et al.

(10) Patent No.: US 8,076,358 B2
(45) Date of Patent: Dec. 13, 2011

(54) 6-SUBSTITUTED-THIO-2-AMINO-QUINOLINE DERIVATIVES USEFUL AS INHIBITORS OF β-SECRETASE (BACE)

(75) Inventors: Ellen Baxter, Glenside, PA (US); Christopher J. Creighton, San Diego, CA (US); Tianbao Lu, Churchville, PA (US); Allen B. Reitz, Lansdale, PA (US); Charles H. Reynolds, Lansdale, PA (US); Tina Morgan Ross, Royerford, PA (US); Ellen Sieber-McMaster, Langhorne, PA (US)

(73) Assignee: Janssen Pharmaceutica NV (BE)

( * ) Notice: Subject to any disclaimer, the term of this patent is extended or adjusted under 35 U.S.C. 154(b) by 286 days.

(21) Appl. No.: 12/360,611

(22) Filed: Jan. 27, 2009

(65) Prior Publication Data

US 2009/0227627 A1  Sep. 10, 2009

Related U.S. Application Data

(60) Provisional application No. 61/024,039, filed on Jan. 28, 2008.

(51) Int. Cl.
  *A61K 31/44* (2006.01)
  *A61P 25/28* (2006.01)
  *C07D 215/38* (2006.01)

(52) U.S. Cl. ..................... 514/313; 546/159
(58) Field of Classification Search .................. None
  See application file for complete search history.

(56) References Cited

U.S. PATENT DOCUMENTS

| | | | |
|---|---|---|---|
| 3,138,595 A | 6/1964 | Osdene et al. |
| 4,001,237 A | 1/1977 | Partyka et al. |
| 4,675,047 A | 6/1987 | Serban et al. |
| 4,739,056 A | 4/1988 | Venuti et al. |
| 4,761,416 A | 8/1988 | Fried et al. |
| 5,387,742 A | 2/1995 | Cordell |
| 5,580,003 A | 12/1996 | Malone et al. |
| 5,612,486 A | 3/1997 | McConlogue et al. |
| 5,672,805 A | 9/1997 | Neve |
| 5,720,936 A | 2/1998 | Wadsworth et al. |
| 5,811,633 A | 9/1998 | Wadsworth et al. |
| 5,877,015 A | 3/1999 | Hardy et al. |
| 5,877,399 A | 3/1999 | Hsiao et al. |
| 6,037,521 A | 3/2000 | Sato et al. |
| 6,071,903 A | 6/2000 | Albright et al. |
| 6,184,435 B1 | 2/2001 | Benson et al. |
| 6,187,922 B1 | 2/2001 | Geen et al. |
| 6,211,428 B1 | 4/2001 | Singh et al. |
| 6,340,783 B1 | 1/2002 | Snow |
| 7,531,545 B2 | 5/2009 | Baxter et al. |
| 7,776,882 B2 | 8/2010 | Baxter et al. |
| 7,786,116 B2 | 8/2010 | Baxter et al. |
| 7,868,022 B2 | 1/2011 | Baxter et al. |
| 7,932,261 B2 | 4/2011 | Baxter et al. |
| 2004/0087548 A1 | 5/2004 | Salvati et al. |
| 2004/0209905 A1 | 10/2004 | Kubo et al. |
| 2005/0171111 A1 | 8/2005 | Angibaud et al. |
| 2006/0074105 A1 | 4/2006 | Ware, Jr. et al. |
| 2006/0079686 A1 | 4/2006 | Baxter et al. |
| 2006/0079687 A1 | 4/2006 | Baxter et al. |
| 2006/0178383 A1 | 8/2006 | Bischoff et al. |

FOREIGN PATENT DOCUMENTS

| | | |
|---|---|---|
| EP | 406958 | 1/1991 |
| EP | 371564 | 7/1995 |
| EP | 1407774 | 4/2004 |
| JP | 63-196573 | 8/1988 |
| JP | 04 011255 | 1/1992 |
| WO | 01/38314 | 5/2001 |
| WO | 01/38315 | 5/2001 |
| WO | 02/100399 | 12/2002 |
| WO | 2004/022523 | 3/2004 |
| WO | 2004/058686 | 7/2004 |
| WO | 2004/063172 | 7/2004 |
| WO | 2005/049585 | 6/2005 |
| WO | 2006/017836 | 2/2006 |
| WO | 2006/017844 | 2/2006 |
| WO | 2006/024932 | 3/2006 |
| WO | 2006/078577 | 7/2006 |
| WO | 2007/050612 | 5/2007 |
| WO | 2007/092846 | 8/2007 |
| WO | 2007/092854 | 8/2007 |
| WO | WO 2007/092854 | * 8/2007 |

OTHER PUBLICATIONS

International Search Report re: PCT/US2009/032126 dated Mar. 30, 2009.
Office Action mailed May 29, 2008 in U.S. Appl. No. 11/197,669.
Office Action mailed Aug. 21, 2008 in U.S. Appl. No. 11/197,669.
Office Action mailed Apr. 29, 2009 in U.S. Appl. No. 11/197,669.
Notice of Allowance mailed Dec. 8, 2009 in U.S. Appl. No. 11/197,669.
Notice of Allowance mailed Nov. 15, 2010 in U.S. Appl. No. 11/197,669.
Office Action mailed May 30, 2008 in U.S. Appl. No. 11/197,608.
Office Action mailed Aug. 20, 2008 in U.S. Appl. No. 11/197,608.
Office Action mailed Apr. 30, 2009 in U.S. Appl. No. 11/197,608.
Notice of Allowance dated Dec. 8, 2009 in U.S. Appl. No. 11/197,608.
Office Action mailed Apr. 28, 2011 in U.S. Appl. No. 11/197,608.
Office Action mailed May 29, 2008 in U.S. Appl. No. 11/197,615.
Office Action mailed Jan. 27, 2009 in U.S. Appl. No. 11/197,615.
Office Action mailed Sep. 29, 2009 in U.S. Appl. No. 11/197,615.
Notice of Allowance mailed Apr. 19, 2010 in U.S. Appl. No. 11/197,615.
Office Action mailed Jun. 19, 2009 in U.S. Appl. No. 11/671,681.
Office Action mailed Sep. 29, 2009 in U.S. Appl. No. 11/671,681.

(Continued)

*Primary Examiner* — Jeffrey S Lundgren
*Assistant Examiner* — Bong-Sook Baek
(74) *Attorney, Agent, or Firm* — Hal B. Woodrow

(57) ABSTRACT

The present invention is directed to 6-substituted-thio-2-amino-quinoline derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

13 Claims, No Drawings

OTHER PUBLICATIONS

Notice of Allowance mailed May 4, 2010 in U.S. Appl. No. 11/671,681.
Notice of Allowance mailed Aug. 23, 2010 in U.S. Appl. No. 11/671,681.
Office Action mailed Jun. 19, 2008 in U.S. Appl. No. 11/671,703.
Office Action mailed Aug. 20, 2008 in U.S. Appl. No. 11/671,703.
Office Action mailed Feb. 12, 2009 in U.S. Appl. No. 11/671,703.
Office Action mailed Jun. 9, 2009 in U.S. Appl. No. 11/671,703.
Notice of Allowance mailed Nov. 19, 2009 in U.S. Appl. No. 11/671,703.
Notice of Allowance mailed Mar. 17, 2010 in U.S. Appl. No. 11/671,703.
Office Action mailed Mar. 24, 2009 in U.S. Appl. No. 11/671,732.
Notice of Allowance mailed Sep. 25, 2009 in U.S. Appl. No. 11/671,732.
Notice of Allowance mailed Jan. 6, 2010 in U.S. Appl. No. 11/671,732.
Notice of Allowance mailed Apr. 16, 2010 in U.S. Appl. No. 11/671,732.
Notice of Allowance mailed Jul. 26, 2010 in U.S. Appl. No. 11/671,732.
Notice of Allowance mailed Dec. 15, 2010 in U.S. Appl. No. 11/671,732.
Notice of Allowance mailed Apr. 14, 2010 in U.S. Appl. No. 12/362,020.
Notice of Allowance mailed Dec. 24, 2009 in U.S. Appl. No. 12/362,020.
Office Action mailed Sep. 10, 2009 in U.S. Appl. No. 12/362,020.
Citron, Trends in Pharm. Sci., vol. 25, Issue 2, Feb. 2004, 92-97.
Cole, et al., Molecular Neurodegeneration 2007, 2:22.
Database Caplus "Online!" Chemical Abstracts Service, Columbus, Ohio, US. Ishikawa, Fumyoshi et al.: "Quinazolineacetic acid derivatives as platelet aggregation inhibitors". XP00236713. (1988).
Ermolieff et al., Biochemistry, (2000) vol. 39, p. 12450.
El Mouedden, M. et al., (Johnson & Johnson Pharmaceutical Research and Development, Division of Janssen Pharmaceutica N.V., Turnhoutseweg 30, Beerse, Belg.), Development of a specific ELISA for the quantitative study of amino-terminally truncated beta-amyloid peptides,. Journal of Neuroscience Methods (2005), 145(1-2), pp. 97-105.
Games, D. et al., (Athena Neurosciences, Inc., South San Francisco, CA, USA), Alzheimer-type neuropathology in transgenic mice overexpressing V717F β-amyloid precursor protein, Nature (London) (1995), 373(6514), pp. 523-527 (V717F mice).
Hamaguchi, et al., Cell. Mol. Life Sci. 63 (2006) 1538-1552.
Hsiao, K. et al., (Dep. Neurology, Univ. Minnesota, Minneapolis, MN, USA), Correlative memory deficits, Aβ elevation, and amyloid plaques in transgenic mice, Science (Washington, D. C.) (1996), 274(5284), pp. 99-102 (Tg2576 mice).
Kienzle, F. et. al., Chemical Abstract, 1983, vol. 98, Abstract No. 143363, (or CAPLUS Accession No. 1983:143363).
Kienzle, F., et al. "1,5-Dihydroimdazoquinazoliones as Blood Platelet Aggregation Inhibitors", European Journal of Medicinal Chemistry, 17(6), 547-556, 1982.
Larner, A.J.: "Secretases as Therapeutic Targets in Alzheimer's Disease: Patents 2000 2004". Expert Opinion On Therapeutic Patents, Ashley Publications, GB, vol. 14, No. 10, 2004, pp. 1403-1420, XP002404250.
Lewczuk, P. et al., (Department of Psychiatry and Psychotherapy, Molecular Neurobiology Lab, University of Erlangen-Nuremberg, Erlangen, Germany), Neurochemical diagnosis of Alzheimer's dementia by CSF Aβ42, Aβ42/Aβ40 ratio and total tau, Neurobiology of Aging (2004), 25(3), pp. 273-281.
Lins, H. et al., (Department of Neurology, Otto-von-Guericke-University, Magdeburg, Germany), Immunoreactivities of amyloid β peptide(1-42) and total τ protein in lumbar cerebrospinal fluid of patients with normal pressure hydrocephalus, Journal of Neural Transmission (2004), 111(3), pp. 273-280.

Neve, R. L. et al., (Dep. Genetics, Harvard Medical School and McLean Hospital, Belmont, MA, USA), Transgenic mice expressing APP-C100 in the brain, Neurobiology of Aging (1996), 17(2), pp. 191-203 (APP-C100 mice).
Oddo, S. et al, (Department of Neurobiology and Behavior, University of California, Irvine, Irvine, CA, USA), Triple-transgenic model of Alzheimer's disease with plaques and tangles: Intracellular Aβ and synaptic dysfunction, Neuron (2003), 39(3), pp. 409-421 (APP Triple Transgenic Mice).
Olsson, A. et al., (Sahlgrenska University Hospital, Experimental Neuroscience Section, Institute of Clinical Neuroscience, Goteborg University, Moelndal, Sweden), Measurement of α- and β-secretase cleaved amyloid precursor protein in cerebrospinal fluid from Alzheimer patients, Experimental Neurology (2003), 183(1), pp. 74-80.
Ruberti et al., (Neuroscience Program, International School for Advanced Studies (SISSA), Trieste, Italy), Phenotypic knockout of nerve growth factor in adult transgenic mice reveals severe deficits in basal forebrain cholinergic neurons, cell death in the spleen, and skeletal muscle dystrophy, Journal of Neuroscience (2000), 20(7), pp. 2589-2601 (AD11 mice).
Schoonenboom, N. S. et al., Amyloid β 38, 40, and 42 species in cerebrospinal fluid: More of the same?, Annals of Neurology (2005), 58(1), pp. 139-142.
Sirinathsinghji, D. J. S. (Merck Sharp and Dohme Research Laboratories, Neuroscience Research Centre, Essex, UK.), Transgenic mouse models of Alzheimer's disease, Biochemical Society Transactions (1998), 26(3), pp. 504-508.
Van Leuven, F. (Experimental Genetics Group, Center for Human Genetics, Flemish Institute for Biotechnology (VIB), K.U.Leuven, Louvain, Belg.), Single and multiple transgenic mice as models for Alzheimer's disease, Progress in Neurobiology (Oxford) (2000), 61(3), pp. 305-312.
Vanderstichele, H. et al., (Innogenetics NV, Ghent, Belg.), Standardization of measurement of β-amyloid(1-42) in cerebrospinal fluid and plasma, Amyloid (2000), 7(4), pp. 245-258.
Venuti, M., et al 'Inhibitors of Cyclic AMP Phosphodiestrase 2 Structural Variations of N-Cyclohexyl-N-Methyl-4-(1,2,3,5-Tetrahydro-2-Oxoimidazo 2,1-B Quinazo-7-yl-Oxybutyramids J. Medicinal Chemistry, American Chemical Society, vol. 30, No. 2, 1987, pp. 303-318.
Wahlund, L.-O et al., (Karolinska Institute, Section of Geriatric Medicine, Department of Clinical Neuroscience and Family Medicine, Huddinge University Hospital, Stockholm, Sweden), Cerebrospinal fluid biomarkers for disease stage and intensity in cognitively impaired patients, Neuroscience Letters (2003), 339(2), pp. 99-102.
Webb, T. Improved Synthesis of Symmetrical and Unsymmetrical 5,11-Methandibenzo'b.f.1,5-iazocines. Readily Available lnanoscale Structural Units, Journal of Organic Chemistry, vol. 55, No. 1, 1990, pp. 363-365.
Bakke, J. M.; Lorentzen, G. B. Acta Chem. Scand. B 1974, 28, 650.
Baumgarth, M.; Beier, N.; Gericke, R. J. Med. Chem. 1998, 41, 3736.
Burk, M. J.; Gross, M. F.; Martinez, J. P. J. Am. Chem. Soc. 1995, 117, 9375.
Deloux, L.; Srebnik, M. J. Org. Chem. 1994, 59, 6871.
Fernandez et al., Org. Biomol. Chem., 2003, 1, 767-771.
Ford et al., J. Med. Chem. 1985, 28, 164.
Hintermann, T.; Gademann, K.; Jaun, B. Seebach, D. Hely. Chim. Acta 1998, 81, 983.
Hu, Y.-Z., Zhang, G., and Thummel, R.P., Org. Lett., vol. 5, 2003, p. 2251.
Jung, M. E.; Lam, P. Y.-S.; Mansuri, M. M.; Speltz, L. M. J. Org. Chem. 1985, 50, 1087.
Jung, M.E. and Dansereau, S.M.K., Heterocycles, vol. 39, 1994, p. 767.
Katritzky, A.R., Chassaing, C., Toader D. and Gill, K., J. Chem. Research, (S), 1999, pp. 504-505.
Katritzky, A.R., Lang, H., Wang, Z., Zhang, Z. and Song, H., J. Org. Chem., 60, 1990, pp. 7619-7624.
Lhermitte, F.; Carboni, B. Synlett, 1996, 377.

Matsubara, S.; Otake, Y.; Hashimoto, Y.; Utimoto, K. Chem. Lett. 1999, 747.

Miyaura, N.; Suzuki, A. Chem. Rev. 1995, 95, 2457.

Osdene, Thomas S. et al. Journal of Medicinal Chemistry (1967), 10(2), 165-7.

Smrcina, M.; Majer, P.; Majerová, E.; Guerassina, T. A.; Eissenstat, M. A. Tetrahedron 1997, 53, 12867.

Suzuki, A. J. Organomet. Chem. 1999, 576, 147.

Takai, K.; Shinomiya, N.; Kaihara, H.; Yoshida, N.; Moriwake, T. Synlett 1995, 963.

Vetelino, M.G. and Coe, J.W., Tetrahedron Lett., 35(2), 1994, pp. 219-222.

Yang, D.; Yip, Y.-C.; Jiao, G.-S.; Wong, M.-K. Org. Synth. 2000, 78, 225.

* cited by examiner

6-SUBSTITUTED-THIO-2-AMINO-QUINOLINE DERIVATIVES USEFUL AS INHIBITORS OF β-SECRETASE (BACE)

CROSS REFERENCE TO RELATED APPLICATIONS

This application claims the benefit of U.S. Provisional Application 61/024,039, filed on Jan. 28, 2008, which is incorporated by reference herein in its entirety.

FIELD OF THE INVENTION

The present invention is directed to 6-substituted-thio-2-amino-quinoline derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibillary tangles which are generated by hyperphosphorylation of tau protein and amyloid plaques which form by aggregation of β-amyloid$_{1-42}$ (Aβ$_{1-42}$) peptide. Aβ$_{1-42}$ forms oligomers and then fibrils, and ultimately amyloid plaques. The oligomers and fibrils are believed to be especially neurotoxic and may cause most of the neurological damage associated with AD. Agents that prevent the formation of Aβ$_{1-42}$ have the potential to be disease-modifying agents for the treatment of AD. Aβ$_{1-42}$ is generated from the amyloid precursor protein (APP), comprised of 770 amino acids. The N-terminus of Aβ$_{1-42}$ is cleaved by β-secretase (BACE), and then γ-secretase cleaves the C-terminal end. In addition to Aβ$_{1-42}$, γ-secretase also liberates Aβ$_{1-40}$ which is the predominant cleavage product as well as Aβ$_{1-38}$ and Aβ$_{1-43}$. Thus, inhibitors of BACE would be expected to prevent the formation of Aβ$_{1-42}$ as well as Aβ$_{1-40}$, Aβ$_{1-38}$ and Aβ$_{1-43}$ and would be potential therapeutic agents in the treatment of AD.

SUMMARY OF THE INVENTION

The present invention is directed to a compound of formula (I)

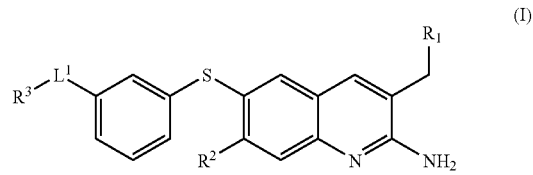

(I)

wherein $R^1$ is selected from the group consisting of $C_{1-4}$alkyl, $C_{3-8}$cycloalkyl, 5-6 membered heteroaryl, —($C_{1-4}$alkyl)-(5-6 membered heteroaryl), 5-6 membered heterocycloalkyl and —($C_{1-4}$alkyl)-5-6 membered heterocycloalkyl;

$R^2$ is selected from the group consisting of hydrogen and halogen;

$L^1$ is selected from the group consisting of —$CH_2$—$NR^A$, —$CH_2CH_2$—$NR^A$, —$CH_2$—O— and —$CH_2$—S—; wherein $R^A$ is selected from the group consisting of hydrogen, $C_{1-4}$alkyl, —C(O)—$C_{1-4}$alkyl, —C(O)O—$C_{1-4}$alkyl and —$SO_2$—$C_{1-4}$alkyl;

$R^3$ is selected from the group consisting of $C_{1-4}$alkyl, carboxy substituted $C_{1-4}$alkyl, $C_{4-8}$cycloalkyl, —($C_{1-4}$alkyl)-$C_{4-8}$cycloalkyl, partially unsaturated carbocyclyl, —($C_{1-4}$alkyl)-(partially unsaturated carbocyclyl), aryl, —($C_{1-4}$alkyl)-aryl, heteroaryl, —($C_{1-4}$alkyl)-heteroaryl, heterocycloalkyl and —($C_{1-4}$alkyl)-heterocycloalkyl; wherein the $C_{4-8}$cycloalkyl, aryl, heteroaryl or heterocycloalkyl, whether alone or as part of a substituent group is optionally substituted with one or more substituents independently selected from the group consisting of halogen, hydroxy, carboxy, $C_{1-4}$alkyl, fluorinated $C_{1-4}$alkyl, —$C_{1-4}$alkoxy-, fluorinated —$C_{1-4}$alkoxy, —$C_{1-4}$alkyl-OH, —$C_{1-4}$alkyl-$CO_2$H and phenyl;

alternatively, $R^A$ and $R^3$ are taken together with the nitrogen atom to which they are bound to form a ring selected from the group consisting of 5 to 6 membered heteroaryl and 5 to 6 membered heterocycloalkyl;

and pharmaceutically acceptable salts thereof.

The present invention is further directed to the compounds of formula (II-a)

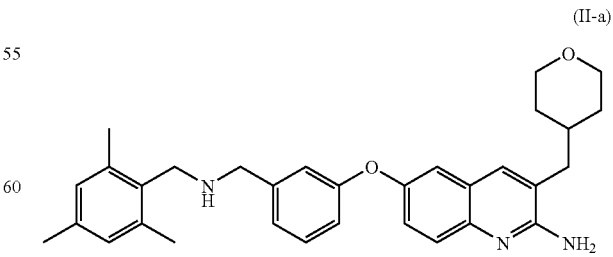

(II-a)

and pharmaceutically acceptable salts thereof. The present invention is further directed to the compounds of formula (II-b)

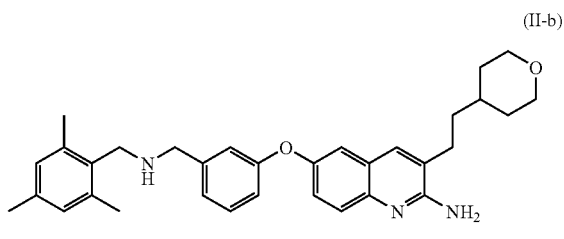

(II-b)

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the β-secretase enzyme, comprising administering to a subject in need thereof a therapeutically effective amount of any of the compounds or pharmaceutical compositions described above.

Further exemplifying the invention are methods of inhibiting the β-secretase enzyme, comprising administering to a subject in need thereof a therapeutically effective amount of any of the compounds or pharmaceutical compositions described above.

An example of the invention is a method of treating a disorder selected from the group consisting of Alzheimer's disease (AD), mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is the use of any of the compounds described above in the preparation of a medicament for treating: (a) Alzheimer's Disease (AD), (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I)

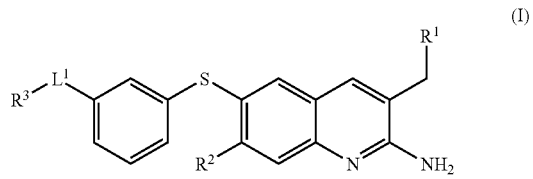

(I)

wherein $R^1$, $R^2$, $L^1$ and $R^3$ are as herein defined, and pharmaceutically acceptable salts thereof; the compound of formula (II-a)

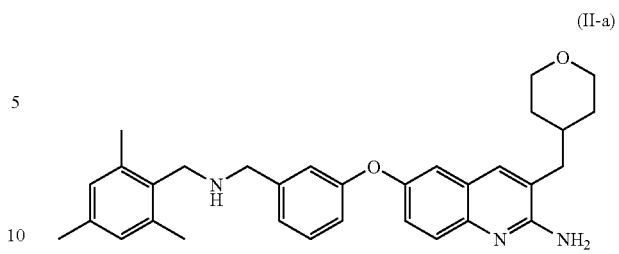

(II-a)

and pharmaceutically acceptable salts thereof; and the compound of formula (II-b)

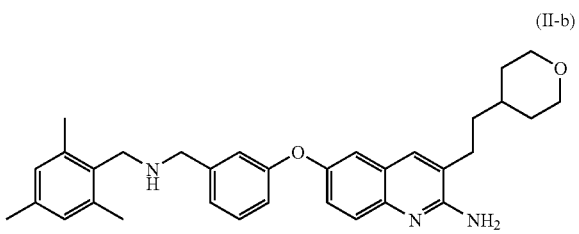

(II-b)

and pharmaceutically acceptable salts thereof. The compounds of formula (I), the compound of formula (II-a), the compound of formula (II-b) and the compound of formula (II-c) are inhibitors of the β-secretase enzyme (also known as β-site cleaving enzyme, BACE, BACE1, Asp2 or memapsin 2), and are useful in the treatment of Alzheimer's disease (AD), mild cognitive impairment (MCI), senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, $R^1$ is selected from the group consisting of $C_{3-8}$cycloalkyl, 5-6 membered heteroaryl, —($C_{1-4}$alkyl)-(5-6 membered heteroaryl), 5-6 membered heterocycloalkyl and —($C_{1-4}$alkyl)-5-6 membered heterocycloalkyl. In another embodiment of the present invention, $R^1$ is selected from the group consisting of 5 to 6 membered heterocycloalkyl. In another embodiment of the present invention, $R^1$ is tetrahydropyranyl.

In an embodiment of the present invention, $R^2$ is selected from the group consisting of hydrogen and halogen. In another embodiment of the present invention, $R^2$ is selected from the group consisting of hydrogen, fluoro, chloro and bromo. In another embodiment of the present invention, $R^2$ is selected from the group consisting of hydrogen and fluoro.

In an embodiment of the present invention, $L^1$ is selected from the group consisting of —$CH_2$—$NR^A$—, —$CH_2CH_2$—$NR^A$—, —$CH_2$—O— and —$CH_2$—S—; wherein $R^A$ is selected from the group consisting of hydrogen, $C_{1-4}$alkyl and —C(O)O—$C_{1-4}$alkyl.

In another embodiment of the present invention, $L^1$ is selected from the group consisting of —$CH_2$—$NR^A$—, —$CH_2CH_2$—$NR^A$—, —$CH_2$—O— and —$CH_2$—S—; wherein $R^A$ is hydrogen. In another embodiment of the present invention, $L^1$ is selected from the group consisting of —$CH_2$—NH—, —$CH_2CH_2$—NH—, —$CH_2$—O— and —$CH_2$—S—. In another embodiment of the present invention, $L^1$ is selected from the group consisting of —$CH_2$—NH—, —$CH_2CH_2$—NH— and —$CH_2$—S—. In another embodiment of the present invention, $L^1$ is —$CH_2$—NH—.

In an embodiment of the present invention, $R^3$ is selected from the group consisting of $C_{1-4}$alkyl, carboxy substituted $C_{1-4}$alkyl, $C_{4-8}$cycloalkyl, —($C_{1-4}$alkyl)-$C_{4-8}$cycloalkyl, aryl, —($C_{1-4}$alkyl)-aryl, heteroaryl, —($C_{1-4}$alkyl)-heteroaryl, heterocycloalkyl and —($C_{1-4}$alkyl)-heterocycloalkyl; wherein the $C_{4-8}$cycloalkyl, aryl, heteroaryl or heterocycloalkyl, whether alone or as part of a substituent group is optionally substituted with one or more substituents independently selected from the group consisting of halogen, $C_{1-4}$alkyl, fluorinated $C_{1-4}$alkyl, —$C_{1-4}$alkoxy-, fluorinated —$C_{1-4}$alkoxy, —$C_{1-4}$alkyl-OH, —$C_{1-4}$alkyl-$CO_2$H and phenyl. Preferably, the $C_{4-8}$cycloalkyl, aryl, heteroaryl or heterocycloalkyl, whether alone or as part of a substituent group is optionally substituted with one or more substituents independently selected from the group consisting of halogen, $C_{1-4}$alkyl, fluorinated $C_{1-4}$alkyl, —$C_{1-4}$alkoxy-, fluorinated —$C_{1-4}$alkoxy, —$C_{1-4}$alkyl-OH, —$C_{1-4}$alkyl-$CO_2$H and optionally further substituted with one phenyl.

In another embodiment of the present invention, $R^3$ is selected from the group consisting of carboxy substituted $C_{1-4}$alkyl, $C_{3-6}$cycloalkyl, aryl, —($C_{1-4}$alkyl)-aryl and —($C_{1-4}$alkyl)-(5 to 6 membered heteroaryl); wherein the $C_{3-6}$cycloalkyl is optionally substituted with one phenyl; and wherein the aryl or —($C_{1-4}$alkyl)-aryl is optionally substituted with one to three substituents independently selected from the group consisting of halogen, $C_{1-4}$alkyl, fluorinated $C_{1-4}$alkyl, $C_{1-4}$alkoxy, and —$C_{1-2}$alkyl-$CO_2$H.

In another embodiment of the present invention, $R^3$ is selected from the group consisting of 1-(1-carboxy-n-butyl), 1S*-(2S*-phenyl)-cyclopropyl, 3-(carboxymethyl)-phenyl, 2,4,6-trimethyl-phenyl, 2-ethoxy-benzyl, 4-trifluoromethyl-benzyl, 2,6-difluoro-benzyl, 2,5-difluoro-benzyl, 2,4-dichloro-benzyl, 2,6-dichloro-benzyl, 2,4-dimethyl-benzyl, 2,5-dimethyl-benzyl, 2,4-dimethoxy-benzyl, 2,4,6-trimethyl-benzyl, 4-imidazolyl-ethyl- and 2-pyridyl-methyl-. In another embodiment of the present invention, $R^3$ is selected from the group consisting of 3-(carboxymethyl)-phenyl, 2-ethoxy-benzyl, 4-trifluoromethyl-benzyl, 2,6-difluoro-benzyl, 2,5-difluoro-benzyl, 2,4-dichloro-benzyl, 2,4-dimethyl-benzyl, 2,4-dimethoxy-benzyl and 2,4,6-trimethyl-benzyl.

In another embodiment of the present invention, $R^3$ is selected from the group consisting of 2-ethoxy-benzyl, 2,6-difluoro-benzyl, 2,5-difluoro-benzyl, 2,4-dichloro-benzyl, 2,4-dimethyl-benzyl and 2,4,6-trimethyl-benzyl.

In an embodiment of the present invention, $L^1$ is —$CH_2$—$NR^A$ and $R^A$ and $R^3$ are taken together with the nitrogen atom to which they are bound to form a ring selected from the group consisting of 5 to 6 membered heterocycloalkyl. In another embodiment of the present invention, $L^1$ is —$CH_2$—$NR^A$— and $R^A$ and $R^3$ are taken together with the nitrogen atom to which they are bound to form a 6 membered heterocycloalkyl. In another embodiment of the present invention, $L^1$ is —$CH_2$—$NR^A$— and $R^A$ and $R^3$ are taken together with the nitrogen atom to which they are bound to form 1-piperazinyl.

Additional embodiments of the present invention, include those wherein the substituents selected for one or more of the variables defined herein (i.e. $R^1$, a, $R^2$, $L^1$ and $R^3$) are independently selected to be any individual substituent or any subset of substituents selected from the complete list as defined herein. In another embodiment of the present invention is any single compound or subset of compounds selected from the representative compounds listed in Tables 1-2 below.

Representative compounds of the present invention are as listed in Table 1 to 2 below. Unless otherwise noted, wherein a stereogenic center is present in the listed compound, the compound was prepared as a mixture of stereo-configurations. Where a stereogenic center is present, the S*- and R*- designations are intended to indicate that the exact stereo-configuration of the center has not been determined.

TABLE 1

Representative Compounds of Formula (I)

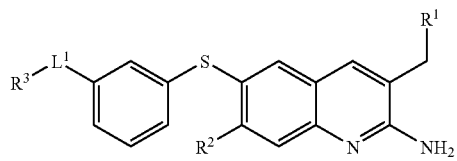

| ID No | $R^1$ | $R^2$ | $L^1$ | $R^3$ |
|---|---|---|---|---|
| 1 | 4-tetrahydro-pyranyl | hydrogen | —$CH_2$—NH— | 2,4,6-trimethyl-benzyl |
| 2 | 4-tetrahydro-pyranyl | hydrogen | —$CH_2$—NH— | 2,4,6-trimethyl-phenyl |
| 3 | 4-tetrahydro-pyranyl | hydrogen | —$CH_2$—NH— | 4-imidazolyl-ethyl |
| 4 | 4-tetrahydro-pyranyl | hydrogen | —$CH_2$—NH— | 2,6-difluoro-benzyl |
| 5 | 4-tetrahydro-pyranyl | hydrogen | —$CH_2$—NH— | 2-pyridyl-methyl |
| 6 | 4-tetrahydro-pyranyl | hydrogen | —$CH_2$—NH— | 2,4-dimethyl-benzyl |
| 7 | 4-tetrahydro-pyranyl | hydrogen | —$CH_2$—NH— | 2,4-dimethoxy-benzyl |
| 8 | 4-tetrahydro-pyranyl | hydrogen | —$CH_2$—NH— | 2,5-difluoro-benzyl |
| 9 | 4-tetrahydro-pyranyl | hydrogen | —$CH_2$—NH— | 2,4-dichloro-benzyl |
| 10 | 4-tetrahydro-pyranyl | hydrogen | —$CH_2$—NH— | 2-ethoxy-benzyl |
| 11 | 4-tetrahydro-pyranyl | hydrogen | —$CH_2$—NH— | 2,6-dichloro-benzyl |
| 12 | 4-tetrahydro-pyranyl | hydrogen | —$CH_2$—NH— | 4-trifluoromethyl-benzyl |
| 13 | 4-tetrahydro-pyranyl | hydrogen | —$CH_2$—NH— | 1-(1-carboxy-n-butyl) |
| 14 | 4-tetrahydro-pyranyl | hydrogen | —$CH_2$—NH— | 1S*-(2S*-phenyl)-cyclopropyl |
| 16 | 4-tetrahydro-pyranyl | hydrogen | —$CH_2$—O— | 2,5-dimethyl-benzyl |
| 17 | 4-tetrahydro-pyranyl | hydrogen | —$CH_2$—S— | 3-(carboxymethyl)-phenyl |
| 18 | 4-tetrahydro-pyranyl | fluoro | —$CH_2$—NH— | 2-ethoxy-benzyl |
| 19 | 4-tetrahydro-pyranyl | hydrogen | —$CH_2CH_2$—NH— | 2,6-difluoro-benzyl |
| 20 | 4-tetrahydro-pyranyl | hydrogen | —$CH_2CH_2$—NH— | 2-ethoxy-benzyl |
| 21 | 4-tetrahydro-pyranyl | hydrogen | —$CH_2CH_2$—NH— | 2-pyridyl-methyl |

| ID No | $R^1$ | $R^2$ | -$L^1$-$R^3$ |
|---|---|---|---|
| 15 | 4-tetrahydro-pyranyl | hydrogen | —$CH_2$-(1-piperazinyl) |

TABLE 2

Additional Compounds of the Present Invention

Compound (II-a)

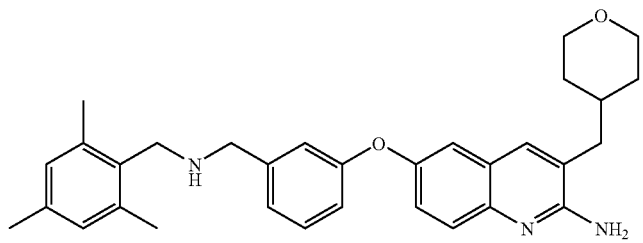

Compound (II-b)

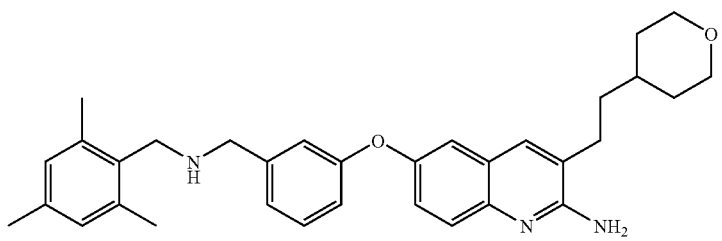

As used herein, unless otherwise noted, the term "halogen" shall mean chlorine, bromine, fluorine and iodine. Preferably, the halogen is fluoro or chloro. More preferably, the halogen is fluoro.

As used herein, unless otherwise noted, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl, isopentyl, hexyl, heptyl, octyl, nonyl, decyl, and the like. Similarly, the term "$C_{1-4}$alkyl" shall include straight and branched chains comprising one to four carbon atoms.

As used herein, the term "fluorinated $C_{1-4}$alkyl" shall mean any $C_{1-4}$alkyl group as defined above substituted with at least one fluoro atom, preferably one to three fluoro atoms. Suitable examples include but are not limited to —$CF_3$, —$CH_2$—$CF_3$, —$CH_2$—$CF_3$, —$CF_2$—$CF_2$—$CF_2$—$CF_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the term "fluorinated $C_{1-4}$alkoxy" shall mean any $C_{1-4}$alkoxy group as defined above substituted with at least one fluoro atom, preferably one to three fluoro atoms. Suitable examples include but are not limited to —$OCF_3$, —$OCH_2$—$CF_3$, —$OCH_2$—$CF_3$, —$OCF_2$—$CF_2$—$CF_2$—$CF_3$, and the like.

As used herein, unless otherwise noted, the term "cycloalkyl" shall mean any stable monocyclic, bicyclic, polycyclic, bridged or spiro-bound, saturated ring system. Suitable examples include, but are not limited to, cyclopropyl, cyclobutyl, cyclopentyl, cyclohexyl, cycloheptyl, cyclooctyl, norboranyl, adamantyl, spiropentane, 2,2,2-bicyclooctyl, and the like. Further, the term "$C_{3-8}$cycloalkyl" shall mean a cycloalkyl as herein defined containing 3 to 8 carbon atoms. Unless otherwise noted, "cycloalkyl" groups do not contain N, O or S heteroatoms.

As used herein, unless otherwise noted, the term "partially unsaturated carbocyclyl" shall mean any stable monocyclic, bicyclic, poycyclic, bridge or spiro-bound ring system containing at least unsaturated bond (i.e. a double or triple bond) or any bicyclic, polycyclic, bridged or spiro-bound, partially aromatic (e.g. benzo-fused) rings system. Suitable examples include, but are not limited to 1,2,3,4-tetrahydro-naphthyl, fluorenyl, 9,10-dihydroanthracenyl, indanyl, and the like. Unless otherwise noted, "partially unsaturated carbocyclyl" groups do not contain N, O or S heteroatoms.

As used herein, unless otherwise noted, "aryl" shall refer to fully conjugated aromatic ring structures such as phenyl, naphthyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Similarly, the term "5 to 6 membered heteroaryl" shall denote any five or six membered monocyclic aromatic ring structure containing at least one heteroatom selected from the group consisting of O, N and S, optionally containing one to three additional heteroatoms independently selected from the group consisting of O, N and S; wherein the 5 to 6 membered heteroaryl may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, 5-tetrazolyl, and the like. Examples of suitably 5 to 6 membered heteroaryl groups include, but are not limited to, furyl, thienyl, pyrrolyl, oxazolyl, thiazolyl, imidazolyl, pyrazolyl, isoxazolyl, isothiazolyl, triazolyl, thiadiazolyl, oxadiazolyl, pyridyl, pyridazinyl, pyrimidinyl, pyrazinyl, triazinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S; or a 7-16 membered saturated, partially unsaturated or partially aromatic polycyclic or bridged ring system containing at least one heteroatom selected from the group consisting of O, N and S, optionally containing one or four additional heteroatoms independently selected from O, N and S. The heterocycloalkyl group may be attached at any heteroatom or carbon atom of the ring such that the result is a stable structure. Similarly, the term "5 to 6 membered heterocycloalkyl" any five to seven membered monocyclic, saturated or partially unsaturated ring structure containing at least one heteroatom selected from the group consisting of O, N and S, optionally containing one to three additional heteroatoms independently selected from the group consisting of O, N and S; wherein the 5 to 6 membered heterocycloalkyl may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, tetrahydropyranyl, azepinyl, 2,3-dihydro-1,4-benzodioxanyl, 1-aza-bicyclo [2.2.2]octanyl, 3-quinuclidinyl, and the like. Examples of suitably 5 to 6 membered heterocyclaolkyl groups include, but are not limited to piperidinyl, piperazinyl, morpholinyl, and the like.

When a particular group is "substituted" (e.g., cycloalkyl, aryl, heterocycloalkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid. Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)-" substituent refers to a group of the formula

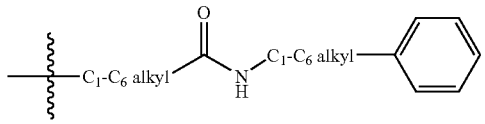

Unless otherwise noted, the position at which substituent groups on the compounds of formula (I) are bound to the 2-amino-quinoline core shall be denoted as follows:

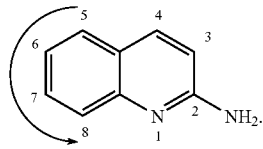

Abbreviations used in the specification, particularly the Schemes and Examples, are as follows
Ac=Acetyl (i.e. —C(O)—$CH_3$)
AD=Alzheimer's Disease
APP=Amyloid Precursor Protein
BACE=Beta Amyloid Site Cleaving Enzyme
$BH_3$.THF=Borane-tetrahydrofuran
DCM=Dichloromethane
DIBAL=Diisobutylamluminium hydride
DMF=N,N-Dimethylformamide
DMSO=Dimethylsulfoxide
EtOAc=Ethyl acetate
EtOH=Ethanol
HEPES=4-(2-Hydroxyethyl)-1-Piperizine Ethane Sulfonic Acid
HPLC=High Pressure Liquid Chromatography
LiHMDS or LiN$(TMS)_2$=Lithium hexamethylisilazide
MCI=Mild Cognitive Impairment
MeOH=Methanol
MTBE=Methyl t-Butyl Ether
$NH_4OAc$=Ammonium Acetate
NMR=Nuclear Magnetic Resonance
OM99-2=4-amino-4-{1-[2-carbamoyl-1-(4-{1-[3-carboxy-1-(1-carboxy-2-phenyl-ethylcarbamoyl)-propylcarbamoyl]-ethylcarbamoyl}-2-hydroxy-1-isobutylpentylcarbamoyl)-ethylcarbamoyl]-2-methyl-propylcarbamoyl}-butyric acid
TFA=Trifluoroacetic Acid
THF=Tetrahydrofuran
TMS=Trimethylsilyl As used herein, unless otherwise noted, the term "isolated form" shall mean that the compound is present in a form which is separate from any solid mixture with another compound(s), solvent system or biological environment. In an embodiment of the present invention, the compound of formula (I), the compound of formula (II-a) or the compound of formula (II-b) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I), the compound of formula (II-a) or the compound of formula (II-b) is present in a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I), the compound of formula (II-a) or the compound of formula (II-b) is present in a form which is substantially free of corresponding salt form(s).

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —SO₂— R" wherein R" is for example benzyl, tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1999.

As used herein, unless otherwise noted, the term "oxygen protecting group" shall mean a group which may be attached to an oxygen atom to protect said oxygen atom from participating in a reaction and which may be readily removed following the reaction. Suitable examples include, but are not limited to methyl, benzyl, trimethylsilyl, tert-butyldimethylsilyl, acetate, 1-ethoxyethyl, and the like. Other suitable nitrogen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

Where the processes for the preparation of the compounds according to the invention give rise to mixture of stereoisomers, these isomers may be separated by conventional techniques such as preparative chromatography or recrystallization. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art.

Compounds of formula (I) wherein -L¹-R³ is —CH₂— NR⁴—R³ may be prepared according to the process outlined in Scheme 1.

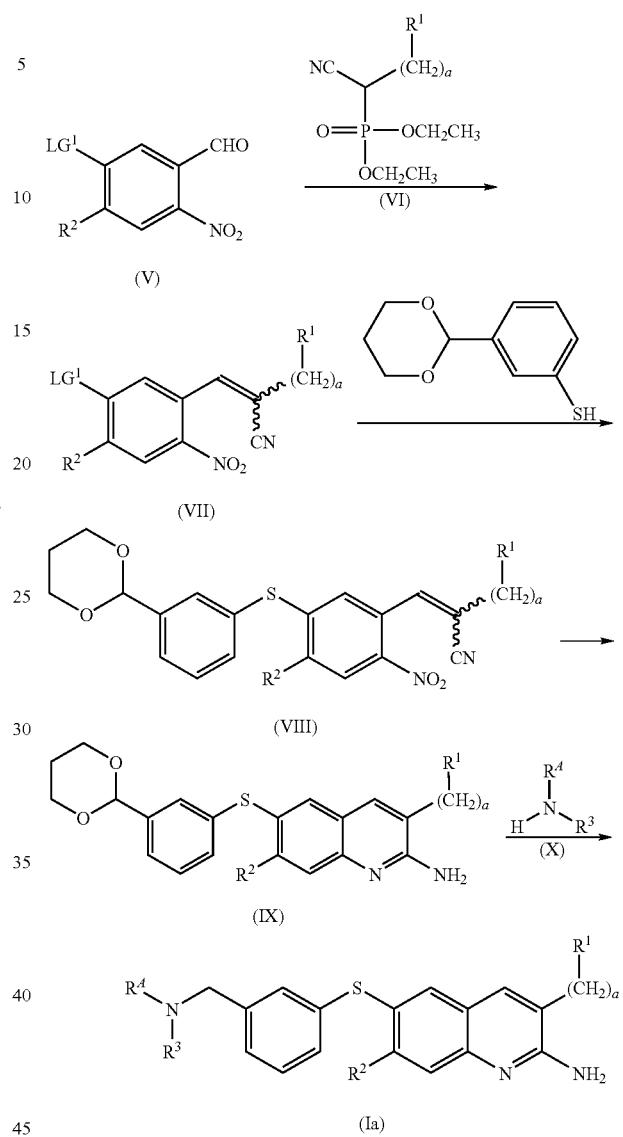

Accordingly, a suitably substituted compound of formula (V), wherein LG¹ is a suitably selected leaving group such as fluoro, chloro, and the like, a known compound or compound prepared by known methods, is reacted with a suitably substituted compound of formula (VI), a known compound or compound prepared by known methods, in the presence of a base such as LiN(TMS)₂, lithium diisopropylamide, NaH, and the like, in an organic solvent such as THF, diethyl ether, and the like, preferably at a temperature in the range of from about 25° C. to about 60° C., to yield the corresponding compound of formula (VII), as a mixture of its corresponding (Z) and (E) isomers.

The compound of formula (VII) is reacted with 3-[1,3] dioxan-2-yl-benzenethiol, a known compound or compound prepared by known methods, in the presence of an inorganic base such as Cs₂CO₃, K₂CO₃, and the like, in an organic solvent such as DMF, DMSO, and the like, preferably at a temperature in the range of from about 25° C. to about 120° C., to yield the corresponding compound of formula (VII).

The compound of formula (VII) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of from about 75° C. to about 100° C., to yield the corresponding compound of formula (IX). Alternatively, the compound of formula (VII) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of from about 75° C. to about 100° C., to yield the corresponding compound of formula (IX).

The compound of formula (IX) is reacted with a suitably substituted compound of formula (X), a known compound or compound prepared by known methods, in the presence of an acid such as acetic acid, anhydrous HCl, and the like, or in the presence of a drying agent, such as Na$_2$SO$_4$, MgSO$_4$, and the like, or in the presence of molecular sieves, in an organic solvent such as acetic acid, DCM, and the like, optionally in a microwave, preferably at a temperature in the range of from about 25° C. to about 150° C., to yield an imine, which is reacted with a reducing agent, such as sodium borohydride, sodium cyanoborohydride, and the like, in an organic solvent, such as methanol, ethanol, and the like, preferably at a temperature in the range of from about 25° C. to about 60° C., to yield the corresponding compound of formula (Ia).

Compounds of formula (I) wherein -L$^1$-R$^3$ is —CH$_2$—NR$^A$-R$^3$ may alternatively may be prepared according to the process as outlined in Scheme 2.

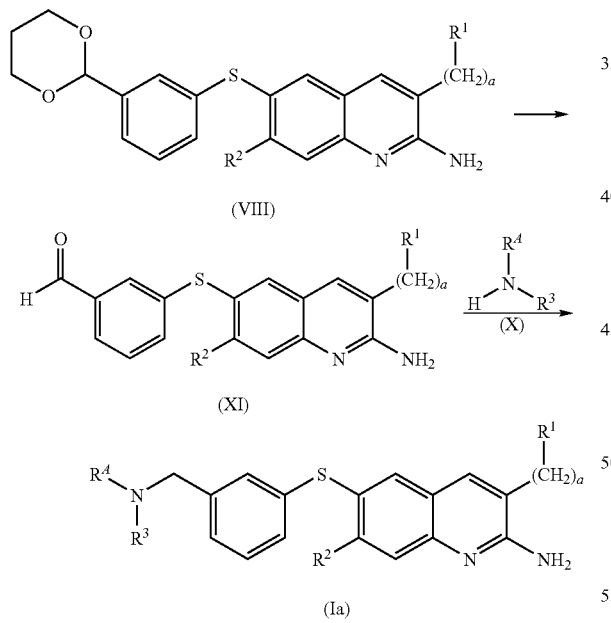

Accordingly, a suitably substituted compound of formula (VII), is reacted with and acid such as HCl, sulfuric acid, trifluoracetic acid, and the like, in an organic solvent such as diethyl ether, THF, DCM, and the like, with water as a co-solvent, preferably at a temperature in the range of from about 0° C. to about 130° C., optionally in a microwave, to yield the corresponding compound of formula (XI).

The compound of formula (XI) is reacted with a suitably substituted compound of formula (X), a known compound or compound prepared by known methods, in the presence of a suitably selected reducing agent, such as sodium triacetoxyborohydride, and the like, in an organic solvent, such as dichloromethane, dichloroethane, THF, and the like, or sodium borohydride in a protic solvent such as methanol or ethanol, or the like, to yield the corresponding compound of formula (Ia). Alternatively, the compound of formula (XI) is reacted with a suitably substituted compound (X), in the presence of sodium cyanoborohydride, in the presence of a catalytic amount of an acid, such as acetic acid, HCl, the like, in an organic solvent, such as methanol, acetonitrile, and the like, to yield the corresponding compound of formula (Ia).

Compounds of formula (I) wherein -L$^1$-R$^3$ is —CH$_2$CH$_2$—NR$^A$—R$^3$ may be prepared according to the process as outlined in Scheme 3, below.

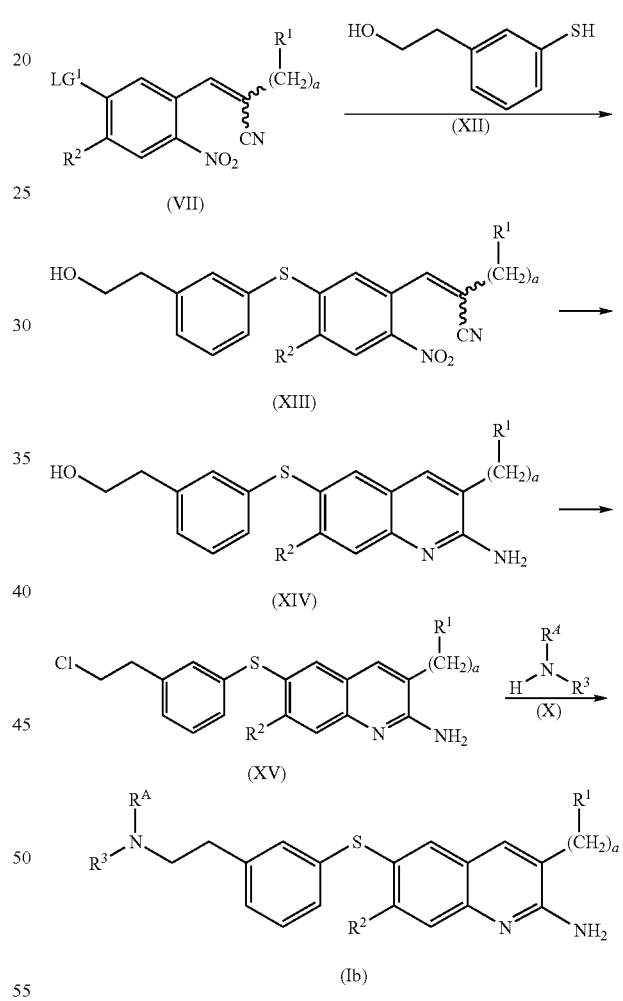

Accordingly, a suitably substituted compound of formula (VII) is reacted with a suitably substituted compound of formula (XII), a known compound or compound prepared by known methods, in the presence of a base such as Cs$_2$CO$_3$, K$_2$CO$_3$, and the like, in an organic solvent such as DMF, DMSO, and the like, preferably at a temperature in the range of from about 25° C. to about 120° C., to yield the corresponding compound of formula (XIII).

The compound of formula (XIII) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of from about 75° C. to about 100° C., to yield the corresponding compound of formula (XIV).

The compound of formula (XIV) is reacted with a chlorinating agent, such as thionyl chloride, phosphorus oxychloride, and the like, optionally with a base, such as pyridine, and the like, in an organic solvent, such as toluene, benzene, chloroform, methylene chloride, and the like, in a temperature range of 0° C. to 80° C., preferably in the range of 25° C. to 60° C., to yield the corresponding compound of formula (XV). Alternatively, compound of formula (XV) is reacted with a chlorinating agent, such as mesyl chloride, and the like, with a base, such as triethylamine, diisopropylethylamine, and the like, in an organic solvent, such as THF, dichloromethane, chloroform, and the like, in a temperature range of 0° C. to 60° C., preferably in the range of 25° C. to 40° C., to yield the corresponding compound of formula (XV).

The compound of formula (XV) is reacted with a compound of formula (X) in the presence of a base, such as triethylamine, diisopropylethylamine, potassium carbonate, and the like, in an organic solvent, such as THF, acetonitrile, DMF, DMSO, and the like, optionally with an iodide source, such as sodium iodide, potassium iodide, and the like, optionally in the presence of microwaves, in a temperature range of 25° C. to 150° C., preferably in the range of 50° C. to 100° C., to yield the corresponding compound of formula (Ib).

One skilled in the art will recognize that compounds of formula (XVI)

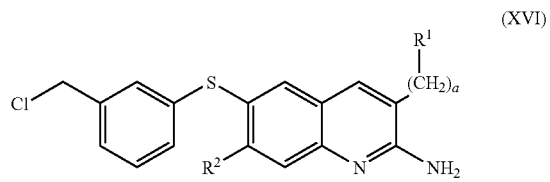

(XVI)

may be similarly prepared according to the procedure as outlined in Scheme 2 above by substituting the compound of formula (XVII)

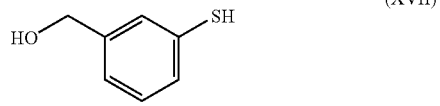

(XVII)

for the compound of formula (XII).

Compounds of formula (I) wherein -$L^1$-$R^3$ is —$CH_2$—O—$R^3$ may alternatively may be prepared according to the process as outlined in Scheme 4.

Scheme 4

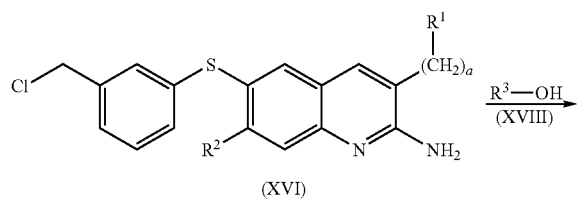

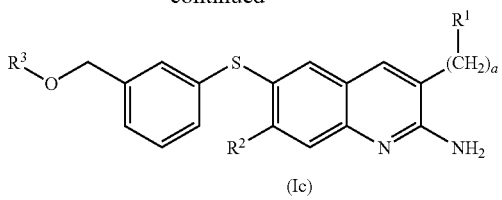

(Ic)

The compound of formula (XVI) is reacted with a suitably substituted compound of formula (XVIII) in the presence of a base such as sodium hydride, sodium hydroxide, and the like, optionally with an iodide source, such as tetrabutyl ammonium iodide, potassium iodide, and the like, in an organic solvent, such as THF, DMF, and the like, in a temperature range of 0° C. to 60° C., preferably in the range of 25° C. to 40° C., to yield the corresponding compound of formula (Ic).

Compounds of formula (I) wherein -$L^1$-$R^3$ is —$CH_2$—S—$R^3$ may alternatively may be prepared according to the process as outlined in Scheme 5.

Scheme 5

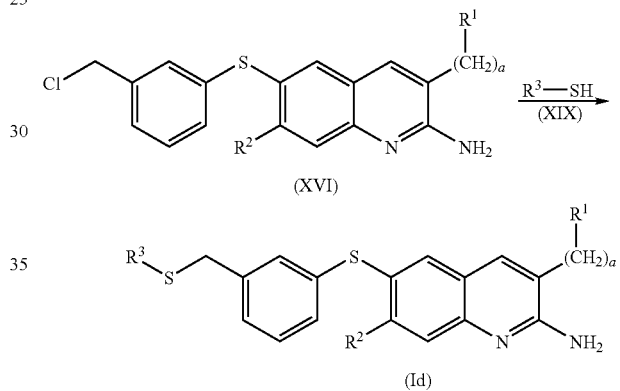

Accordingly, the compound of formula (XVI) is reacted with a suitably substituted compound of formula (XIX) in the presence of a base such as sodium hydroxide, potassium hydroxide, and the like, in an organic solvent, such as EtOH, MeOH, and the like, in a temperature range of 0° C. to 60° C., preferably in the range of 0° C. to 25° C., to yield the corresponding compound of formula (Id). Alternatively, the compound of formula (XVI) is reacted with a suitably substituted compound of formula (XIX) in the presence of a base such as sodium hydride, and the like, in an organic solvent, such as THF, diethyl ether, and the like, in a temperature range of 0° C. to 60° C., preferably in the range of 0° C. to 25° C., to yield the corresponding compound of formula (Id).

3-[1,3]Dioxan-2-yl-benzenethiol may be prepared for example, according to the process outlined in Scheme 6, below.

Scheme 6

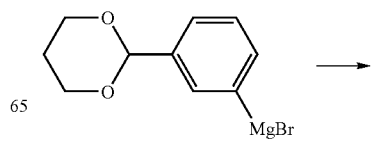

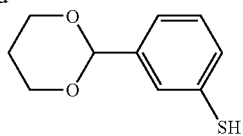

Accordingly, 2-(3-MgBr substituted phenyl)-[1,3]dioxane is reacted with elemental sulfur, in an organic solvent such as THF, diethyl ether, and the like, preferably at a temperature in the range of from about 0° C. to about 40° C., for a period of from about one to about three hours; followed by the addition of a suitably selected reducing agent, such as LiAlH$_4$, NaBH$_4$, and the like, in an organic solvent such as THF, diethyl ether, and the like, preferably at a temperature in the range of from about 0° C. to about 40° C. The preparation of 3-[1,3]dioxan-2-yl-benzenethiol is described in Example 1, which follows herein.

Compounds of formula (VI) are known compounds or compounds which may be prepared according to known methods. For example, compounds of formula (VI) may be prepared according to the process as outlined in Scheme 7, below.

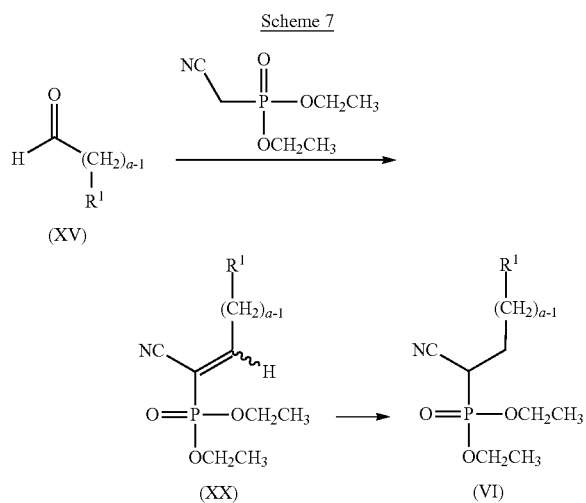

Accordingly, a suitably substituted compound of formula (XV), a known compound or compound prepared by known methods, is reacted with cyanomethyl-phosphonic acid diethyl ester, a known compound, in the presence of an organic amine such as NH$_4$OAc, piperidine, pyridine, and the like, in the presence of an acid such as acetic acid, formic acid, β-alanine, and the like, in an organic solvent such as toluene, ethanol, methanol, and the like, to yield the corresponding compound of formula (XX).

The compound of formula (XX) is reacted with a suitably selected reducing agent, such as sodium borohydride, lithium borohydride, and the like, in an organic solvent, such as methanol, ethanol, and the like, to yield the corresponding compound of formula (VI).

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.1-1000 mg/kg/day, preferably, at a dosage of from about 0.5 to about 500 mg/kg/ day, more preferably, at a dosage of from about 0.5 to about 250 mg/kg/day, more preferably, at a dosage of from about 0.5 to about 100 mg/kg/day, more preferably, at a dosage of from about 1.0 to about 50 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, preferably, from about 0.1 to about 500 mg, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by BACE described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, one or more of the compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of disorders mediated by BACE is required.

The daily dosage of the products may be varied over a wide range from 0.01 to 10,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1-1,000 mg/kg/day, or any range therein, preferably, at a dosage of from about 0.5 to about 500 mg/kg/day, or any range therein, more preferably, at a dosage of from about 0.5 to about 250 mg/kg/day, or any range therein, more preferably, at a dosage of from about 0.5 to about 100 mg/kg/day, or any range therein, more preferably, at a dosage of from about 1.0 to about 50 mg/kg/day or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

3-(Tetrahydro-pyran-4-ylmethyl)-6-{3-[(2,4,6-trimethyl-benzylamino)-methyl]-phenylsulfanyl}-quinolin-2-ylamine (Compound #1)

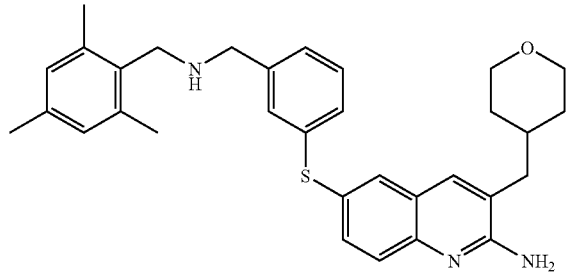

Step A: 1-Cyano-2-(tetrahydro-pyran-4-yl)-vinyl]-phosphonic acid diethyl ester

Tetrahydropyran carboxyaldehyde (10 g, 87.6 mmol), diethyl cyanoacetophosphonate (16.3 g, 92 mmol), acetic acid (3 mL, 50 mmol), ammonium acetate (3 g, 38.9 mmol) were combined in toluene (60 mL), and stirred overnight at room temperature, then heated to 100° C. for two hours and then filtered through MgSO$_4$. The solvent was removed to yield an oil which was purified via silica column chromatography (50% EtOAc/heptane) to yield an oil.

Step B: [1-Cyano-2-(tetrahydro-pyran-4-yl)-ethyl]-phosphonic acid diethyl ester

To a solution of [1-cyano-2-(tetrahydro-pyran-4-yl)-vinyl]-phosphonic acid diethyl ester (7.45 g, 27.1 mmol) in methanol (200 mL) was added sodium borohydride (5 g, 135 mmol, 5 pellets), portion wise over 1.5 hours. The resulting mixture was stirred an additional 2 hours. The solvent was evaporated in vacuo to yield an oil, to which was added 0.1N NaOH and ethyl acetate. The layers were separated, and the organic layer was dried with MgSO$_4$ and filtered. The solvent was removed to yield an oil which was purified via silica column chromatography (50% EtOAc/heptane) to yield an oil.

Step C: 3-[1,3]Dioxan-2-yl-benzenethiol

3-[1,3]Dioxan-2-yl-benzenemagnesium bromide (200 mL, 50 mmol, [0.25 M] in THF) and sulfur (3.67 g, 114 mmol) were stirred at room temperature for 2 h. Lithium aluminum hydride (105 mL, 105 mmol, [1M] in THF) was then added dropwise, and the resulting mixture was stirred at room temperature for 1 hour. The resulting mixture was quenched with 1N HCl and ice, and then extracted with ethyl acetate. The organic layer was filtered through MgSO$_4$ and the solvent removed to yield an oil.

Step D: 3-(5-Fluoro-2-nitro-phenyl)-2-(tetrahydro-pyran-4-ylmethyl)-acrylonitrile

[1-Cyano-2-(tetrahydro-pyran-4-yl)-ethyl]-phosphonic acid diethyl ester (5.4 g, 19.6 mmol) was dissolved in THF (100 mL) and cooled to 0° C. Lithium (bistrimethylsilyl) amide (20 mL, 20 mmol, [1M]) was the added dropwise. The resulting mixture was stirred 20 min, and then 5-fluoro-2-nitro-benzaldehyde (3.31 g, 19.6 mmol) was added. The resulting mixture was stirred at room temperature overnight, then diluted with ethyl acetate and washed with saturated aqueous NaHCO$_3$ solution. The organic phase was separated and dried with MgSO$_4$ and filtered. The solvent was removed to yield an oil which was purified by silica column chromatography (120 g column, 20% EtOAc/heptane) to yield a solid.

Step E: 3-[5-(3-[1,3]-Dioxan-2-yl-phenylsulfanyl)-2-nitro-phenyl]-2-(tetrahydro-Pyran-4-ylmethyl)-acrylonitrile 3-(5-Fluoro-2-nitro-phenyl)-2-(tetrahydro-pyran-4-ylmethyl)-acrylonitrile (1.2 g, 4.07 mmol) and 3-[1,3]dioxan-2-yl-benzenethiol (0.8 g, 4.07 mmol) were added to a mixture of Cs$_2$CO$_3$ (2.78 g, 8.56 mmol) in DMF (100 mL). The resulting mixture was stirred at room temperature overnight, then diluted with ethyl acetate and washed with H$_2$O. The organic phase was separated, dried with MgSO$_4$, and filtered. The solvent was removed to yield an oil, which was purified by silica column chromatography (40% EtOAc/heptane) to yield an oil.

Step F: 6-(3-[1,3]Dioxan-2-yl-phenylsulfanyl)-3-(tetrahydro-pyran-4-ylmethyl)-quinolin-2-ylamine In four μwave tubes, 3-[5-(3-[1,3]dioxan-2-yl-phenylsulfanyl)-2-nitro-phenyl]-2-(tetrahydro-pyran-4-ylmethyl)-acrylonitrile (0.175 g, 0.375 mmol, each tube), Zn (2.5 g, 0.038 mol, each tube), NH$_4$Cl (0.8 g, 0.015 mol, each tube), CH$_3$OH (3 mL, in each tube) and THF (3 mL, in each tube) was reacted via μwave at 300W, 150° C. for 11 min. The resulting mixtures were combined and then filtered through Celite®. The solvent was removed to yield a residue which was purified by reverse phase column chromatography (10-90% CH$_3$CN/H$_2$O/0.1% TFA) to yield a solid.

Step G: 3-(Tetrahydro-pyran-4-ylmethyl)-6-{3-[(2,4,6-trimethyl-benzylamino)-methyl]-phenylsulfanyl}-quinolin-2-ylamine 6-(3-[1,3]Dioxan-2-yl-phenylsulfanyl)-3-(tetrahydro-pyran-4-ylmethyl)-quinolin-2-ylamine (40 mg, 0.1 mmol) was dissolved in acetic acid (1 mL) and then 2,4,6-trimethylbenzyl amine (0.1 g, 0.67 mmol) was added. The resulting mixture was subjected to μwave @ 300W, 100° C. for 12 min. The resulting mixture was evaporated under reduced pressure (high vacuum) overnight. Methanol (2 mL) was added, followed by addition of NaBH₄ (0.2 g, 5.2 mmol, portionwise) over 1.5 h. The solvent was removed to yield a residue, to which was added 0.1 N NaOH (5 ml). The resulting mixture was extracted with chloroform (3×). The organic layers were combined and dried with MgSO₄ and then filtered. The solvent was removed to yield the title compound as a residue, which was purified by reverse phase chromatography (10-90% CH₃CN/H₂O/0.1% TFA). The product containing fractions were treated with 1N HCl (1 mL) to yield the title compound, 3-(tetrahydro-pyran-4-ylmethyl)-6-{3-[(2,4,6-trimethyl-benzylamino)-methyl]-phenylsulfanyl}-quinolin-2-ylamine, as a residue.

MS m/z (ES) MH+=512.4

¹H NMR (300 MHz, CD₃OD)-68.2 (s, 1H), 7.90 (s, 1H), 7.6-7.72 (m, 3H), 7.45-7.6 (m, 3H), 6.95 (s, 2H), 4.35 (s, 2H), 4.18 (s, 2H), 3.9 (m, 2H), 3.35 (m, 2H), 2.68-2.71 (m, 4H), 2.25 (m, 10H), 1.95 (m, 1H), 1.6 (m, 2H), 1.3-1.48 (m, 2H).

Example 2

6-{3-[(2-Ethoxy-benzylamino)-methyl]-phenylsulfanyl}-7-fluoro-3-(tetrahydro-pyran-4-ylmethyl)-quinolin-2-ylamine (Compound #18)

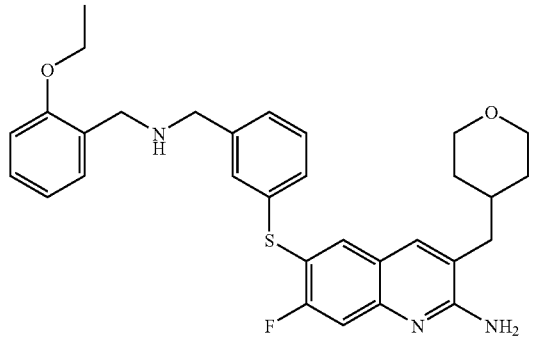

Step A: (4,5-Difluoro-2-nitro-phenyl)-methanol 4,5-Difluoro-2-nitro-benzoic acid (3.05 g, 15 mmol) was combined with THF (20 mL), and then BH₃ THF (35 mL) was added over 15 min. The resulting mixture was stirred overnight at 60° C. and then cooled to room temperature. Methanol was added, and the resulting mixture was stirred 15 min. The solvent was removed to yield an oil, which was purified by silica gel chromatography to yield a residue.

Step B: [5-(3-[1,3]Dioxan-2-yl-phenylsulfanyl)-4-fluoro-2-nitro-phenyl]-methanol 3-[1,3]Dioxan-2-yl-benzenethiol (2.57 g, 14.02 mmol), prepared as described in Example 1, Step C, (4,5-difluoro-2-nitro-phenyl)-methanol (2.65 g, 14.02 mmol), and cesium carbonate (9.1 g, 28 mmol) were combined in DMF (100 mL). The resulting mixture was stirred overnight at room temperature. Water was added, and the resulting mixture was then extracted with ethyl acetate. The organic layer was dried with Na₂SO₄ and filtered, and the solvent was removed to yield an oil, which was purified via silica column chromatography (50% EtOAc/heptane) to yield a solid.

Step C: 5-(3-[1,3]Dioxan-2-yl-phenylsulfanyl)-4-fluoro-2-nitro-benzaldehyde

[5-(3-[1,3]Dioxan-2-yl-phenylsulfanyl)-4-fluoro-2-nitro-phenyl]-methanol (2.22 g, 6.08 mmol) was placed in chloroform (250 mL), and MnO₂ (6.4 g) was added. The resulting mixture was stirred overnight at room temperature. After 18 h of stirring, the mixture was heated at 40° C. for 1 hour. The resulting mixture was worked up by filtration through Celite®. The filtrate was concentrated to yield an oil, which was purified by silica column chromatography (20% EtOAc/heptane) to yield a solid.

Step D: (3-[5-(3-[1,3]Dioxan-2-yl-phenylsulfanyl)-4-fluoro-2-nitro-phenyl]-2-(tetrahydro-pyran-4-ylmethyl)-acrylonitrile

[1-Cyano-2-(tetrahydro-pyran-4-yl)-ethyl]-phosphonic acid diethyl ester (0.614 g, 2.23 mmol), prepared as described in Example 1, Steps A and B, was dissolved in THF (75 mL) and the resulting mixture cooled to 0° C. Lithium (bistrimethylsilyl)amide (2.2 mL, 2.2 mmol, [1M]) was then added dropwise. The resulting mixture was stirred 15 min, and then 5-(3-[1,3]dioxan-2-yl-phenylsulfanyl)-4-fluoro-2-nitro-benzaldehyde (0.6 g, 1.65 mmol) was added. Stirring was continued at room temperature overnight. The resulting mixture was then diluted with ethyl acetate and washed with saturated aqueous NaHCO₃. The organic phase was separated and dried with MgSO₄, and filtered. The solvent was removed to yield an oil, which was used in the next step without further purification.

Step E: 6-(3-[1,3]Dioxan-2-yl-phenylsulfanyl)-7-fluoro-3-(tetrahydro-pyran-4-ylmethyl)-quinolin-2-ylamine In three μwave tubes 3-[5-(3-[1,3]dioxan-2-yl-phenylsulfanyl)-4-fluoro-2-nitro-phenyl]-2-(tetrahydro-pyran-4-ylmethyl)-acrylonitrile (0.25 g, 0.52 mmol, each tube), Zn (3 g, 0.046 mol, each tube), NH₄Cl (0.98 g, 0.018 mol, each tube), CH₃OH (3 mL, in each tube), and THF (1 mL, in each tube) were reacted via μwave @ 300W, 130° C. for 12 min. The resulting mixtures were combined, filtered through Celite®, and the solvent removed to yield a residue, which was purified by silica column chromatography (50% EtOAc/heptanes) to yield a solid.

Step F: 3-[2-Amino-7-fluoro-3-(tetrahydro-pyran-4-ylmethyl)-quinolin-6-ylsulfanyl]-benzaldehyde In a μwave tube, 6-(3-[1,3]dioxan-2-yl-phenylsulfanyl)-7-fluoro-3-(tetrahydro-pyran-4-ylmethyl)-quinolin-2-ylamine (45 mg, 0.1 mmol) was placed with HCl (conc.) (0.5 mL), H₂O (0.5 mL) and diethyl ether (0.2 mL) were reacted via μwave @ 300W, 130° C. for 12 min. The resulting mixture was worked up by removal of solvent to yield a residue, which was purified by silica column chromatography (50% EtOAc/heptanes) to yield a solid.

Step G: 6-{3-[(2-Ethoxy-benzylamino)-methyl]-phenylsulfanyl}-7-fluoro-3-(tetrahydro-pyran-4-ylmethyl)-quinolin-2-ylamine 3-[2-Amino-7-fluoro-3-(tetrahydro-pyran-4-ylmethyl)-quinolin-6-ylsulfanyl]-benzaldehyde (40 mg, 0.1 mmol) was dissolved in methanol (1 mL), and then 2-ethoxybenzyl amine (60 μL, 0.38 mmol) was added. The resulting mixture was subjected to μW @ 300W, 130° C. for 12 min. NaBH₄ (50 mg, 1.3 mmol) was then added portionwise over 1.5 h. The solvent was removed to yield a residue, to which was added 0.1 N NaOH (5 mL). The resulting mixture was extracted with chloroform (3×). The organic layers were combined and dried with MgSO₄ and filtered. The solvent was removed to yield a second residue which was purified on silica gel (2-10% MeOH/dichloromethane) to yield the title compound as a residue.

MS m/z (ES) MH+=532.3

¹H NMR (300 MHz, CD₃OD): δ 8.16 (s, 1H), 7.97 (d, J=7.4 Hz, 1H), 7.3-7.6 (m, 7H), 6.9-7.1 (m, 2H), 4.255 (s, 2H), 4.05-4.23 (m, 6H), 3.9 (m, 2H), 3.3-3.45 (m, 2H), 2.68 (d, J=7.1 Hz, 2H), 1.8-2.0 (br s, 1H), 1.6 (m, 1H), 1.5 (t, 3H), 1.4-1.48 (m, 4H).

Example 3

3-(Tetrahydro-pyran-4-ylmethyl)-6-{3-[(2,4,6-trimethylbenzylamino)-methyl]-phenoxy}-quinolin-2-ylamine (Compound (II-a))

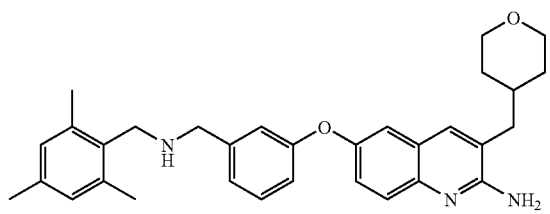

Step A:
3-[(2,4,6-Trimethyl-benzylamino)-methyl]-phenol

3-Hydroxy-benzaldehyde (1.22 g, 0.01 mol) and 2,4,6-trimethyl-benzylamine (1.19 g, 0.01 mol) were added to methanol (10 mL) and the resulting mixture was stirred overnight. Sodium borohydride (0.45 g, 0.012 mol) was then added, and stirring was continued one hour. The resulting mixture was acidified with 2N HCl and then neutralized with saturated aqueous NaHCO₃ solution to yield a gummy solution. The gummy solution was extracted with EtOAc (3×100 mL). The organic layer was washed with brine, dried over sodium sulfate, and concentrated in vacuo to yield a white solid.

MH⁺ 256

Step B: 2-Nitro-5-{3-[(2,4,6-trimethyl-benzylamino)-methyl]-phenoxy}-benzaldehyde The solid prepared as in Step A above (2.44 g, 9.6 mmol), 5-fluoro-2-nitro-benzaldehyde (1.62 g, 9.6 mmol), and cesium carbonate (6.25 g, 19.2 mmol) were taken up into DMF (30 mL) and the resulting mixture stirred at room temperature overnight. Additional 5-fluoro-2-nitro-benzaldehyde (0.30 g, 1.8 mmol) was added, and the resulting mixture was stirred for six hours. The reaction was quenched with water and the resulting mixture extracted with ethyl acetate. The organic layer was washed with brine. The solvent was dried over sodium sulfate and removed in vacuo. The resulting residue was purified on normal phase (EtOAc/heptane) to yield a light yellow oil.

MH⁺ 405

Step C: (Tetrahydro-pyran-4-yl)-acetonitrile; [3-(4-nitro-3-vinyl-phenoxy)-benzyl]-(2,4,6-trimethyl-benzyl)-amine The light yellow oil prepared as in Step B above (1.0 g, 2.5 mmol), [1-cyano-2-(tetrahydro-pyran-4-yl)-ethyl]-phosphonic acid diethyl ester (0.75 g, 2.75 mmol), prepared as described in Example 1, Steps A and B, and 1N LiHMDS in THF (2.75 mL, 2.75 mmol) were taken into THF (25 mL) and the resulting mixture stirred at room temperature overnight. The reaction was quenched with water and the resulting mixture extracted with ethyl acetate. The organic layer was washed with brine. The solvent was dried over sodium sulfate and removed in vacuo. The resulting residue was purified by normal phase chromatography (EtOAc/heptane) to yield an oil.

MH⁺ 526

Step D: 3-(Tetrahydro-pyran-4-ylmethyl)-6-{3-[(2,4,6-trimethyl-benzylamino)-methyl]-phenoxy}-quinolin-2-ylamine The oil prepared as in Step C above (0.56 g, 1.1 mmol), zinc (0.54 g, 8.8 mmol), and ammonium chloride (0.47 g, 8.8 mmol) were taken up in methanol (5 mL) and the resulting mixture stirred at 80° C. for 2.5 hours. The mixture was then filtered, and the solvent was removed in vacuo. The resulting residue was taken into EtOAc and washed with saturated aqueous NaHCO₃ and brine. The organic layer was dried over sodium sulfate and the solvent was removed in vacuo. The resulting second residue was purified on a normal phase column (EtOAc/heptane) to yield the title compound as a white solid.

MH⁺ 496

¹H NMR (300 MHz, CDCl₃): δ1.2-1.4 (m, 2H), 1.5 (d, 3H), 1.7-1.9 (m, 1H), 2.14 (s, 3H), 2.20 (s, 6H), 2.48 (d, 2H), 3.2-3.4 (t, 2H), 3.62 (s, 2H), 3.75 (s, 2H), 3.8-3.9 (m, 2H), 4.68 (s, 2H), 6.7 (s, 2H), 6.8-6.9 (d, 1H), 6.95 (s, 1H), 7.05 (s, 2H), 7.2-7.3 (m, 2H), 7.45 (s, 1H), 7.6 (d, 1H).

Example 4

3-[2-(Tetrahydro-pyran-4-yl)-ethyl]-6-{3-[(2,4,6-trimethylbenzylamino)-methyl]-phenoxy}-quinolin-2-ylamine (Compound (II-b))

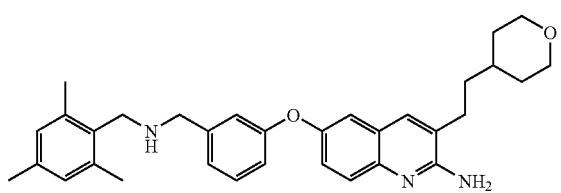

The title compound was similarly prepared as outlined in Example 1 above, substituting [1-cyano-2-(tetrahydro-pyran-4-yl)-propyl]-phosphonic acid diethyl ester for [1-cyano-2-(tetrahydro-pyran-4-yl)-ethyl]-phosphonic acid diethyl ester in Step D, to yield a residue.

MH⁺ 510.4

¹H NMR (300 MHz, CDCl₃): δ1.2-1.4 (m, 2H), 1.4-1.6 (m, 5H), 1.9 (s, 2H), 2.0 (s, 2H), 2.20 (s, 6H), 2.6 (d, 2H), 3.2-3.4

(t, 2H), 3.7-4.0 (m, 6H), 6.6 (s, 2H), 6.9 (d, 1H), 7.2 (s, 1H), 7.25-7.4 (m, 4H), 7.65 (d, 1H), 7.7 (s, 1H), 8.0 (s, 1H), 9.7 (s, 1H).

Example 5

In Vitro BACE Assay

This assay was run by CEREP (Catalog Ref. 761-B, Referred to SOP No. 1C131; ERMOLIEFF, J., LOY, J. A., KOELSCH, G. and TANG, J., Proteolytic activation of recombinant pro-memapsin 2 (pro-BACE) studied with new fluorogenic substrates, Biochemistry, (2000) Vol. 39, p. 12450).

More specifically the assay, run at 50 µL in a 96 well plate, evaluated the effect of test compound on the activity of the human BACE-1 quantified by measuring the formation of Mca-S-E-V-N-L-NH$_2$ from Mca-S-E-V-N-L-D-A-E-F-R-K(Dnp)-R-R—NH$_2$, using a recombinant enzyme.

The test compound, reference compound or water (control) was added to a buffer containing 0.09 M sodium acetate (pH 4.5) and 0.25 µg BACE-1. Compound interference with the fluorimetric detection method due to autofluorescence was then checked by measurements at the wavelengths defined to evaluate the enzyme activity. Thereafter, the reaction was initiated by adding 7.5 µM of the substrate Mca-S-E-V-N-L-D-A-E-F-R-K(Dnp)-R—R—NH$_2$ and the mixture was incubated for 60 min at 37° C. For control basal measurement, the substrate was omitted from the reaction mixture. Immediately after the incubation, the fluorescence intensity emitted by the reaction product Mca-S-E-V-N-L-NH$_2$ was measured at $\lambda$ex=320 nm and $\lambda$em=405 nm using a microplate reader (Ultra, Tecan). The standard inhibitory reference compound was OM99-2, which was tested in each experiment at several concentrations to obtain an inhibition curve from which its IC$_{50}$ value was calculated.

Representative compounds of the present invention were tested as described above, with results as listed in Table 3 below.

TABLE 3

| % Inhibition and IC$_{50}$ | | | |
|---|---|---|---|
| ID No | IC$_{50}$ (µM) | % Inh @1 µM | % Inh @ 10 µM |
| 1 | 0.26 | | 96 |
| 2 | 0.92 | | 94 |
| 3 | | | 26 |
| 4 | 0.40 | | 97 |
| 5 | 0.80 | | 93 |
| 6 | 0.45 | | 98 |
| 7 | 0.38 | | 90 |
| 8 | 0.21 | | 95 |
| 9 | 0.24 | | 98 |
| 10 | 0.30 | | 95 |
| 11 | | | 92 |
| 12 | 0.46 | | 90 |
| 13 | 2.80 | | 63 |
| 14 | | | 89 |
| 15 | | | 35 |
| 16 | 1.20 | | 93 |
| 17 | 0.33 | | 94 |
| 18 | 0.26 | | 95 |
| 19 | | | 96 |
| 20 | 0.14 | | 98 |
| 21 | 0.63 | | 91 |
| (II-a) | 1.20 | | 98 |
| (II-b) | >10 | | 74 |

Representative compounds of the present invention were further tested in various cellular assays. The measured results in these assays were generally consistent with the in vitro results listed above.

Example 6

In Vivo Testing

Compounds of the present invention may be further tested for their effectiveness in the treatment of disorders mediated by the BACE enzyme, for example Alzheimer's disease, by testing the compounds in an in vivo assay, for example, as disclosed in Sirinathsinghji, D. J. S. (Merck Sharp and Dohme Research Laboratories, Neuroscience Research Centre, Essex, UK.), *Transgenic mouse models of Alzheimer's disease*, Biochemical Society Transactions (1998), 26(3), pp 504-508;

Van Leuven, F. (Experimental Genetics Group, Center for Human Genetics, Flemish Institute for Biotechnology (VIB), K. U. Leuven, Louvain, Belg.), *Single and multiple transgenic mice as models for Alzheimer's disease*, Progress in Neurobiology (Oxford) (2000), 61(3), pp 305-312;

Hsiao, K.; Chapman, P.; Nilsen, S.; Eckman, C.; Harigaya, Y.; Younkin, S.; Yang, F.; Cole, G. (Dep. Neurology, Univ. Minnesota, Minneapolis, Minn., USA), *Correlative memory deficits, Aβ elevation, and amyloid plaques in transgenic mice*, Science (Washington, D.C.) (1996), 274(5284), pp 99-102 (Tg2576 mice);

Oddo, S.; Caccamo, A.; Shepherd, J. D.; Murphy, M. P.; Golde, T. E.; Kayed, R.; Metherate, R.; Mattson, M. P.; Akbari, Y.; LaFerla, F. M. (Department of Neurobiology and Behavior, University of California, Irvine, Irvine, Calif., USA), *Triple-transgenic model of Alzheimer's disease with plaques and tangles: Intracellular Aβ and synaptic dysfunction*, Neuron (2003), 39(3), pp 409-421 (APP Triple Transgenic Mice);

Ruberti, F.; Capsoni, S.; Comparini, A.; Di Daniel, E.; Franzot, J.; Gonfloni, S.; Rossi, G.; Berardi, N.; Cattaneo, A. (Neuroscience Program, International School for Advanced Studies (SISSA), Trieste, Italy), *Phenotylic knockout of nerve growth factor in adult transgenic mice reveals severe deficits in basal forebrain cholinergic neurons, cell death in the spleen, and skeletal muscle dystrophy*, Journal of Neuroscience (2000), 20(7), pp 2589-2601 (AD11 mice);

Games, D.; Adams, D.; Alessandrini, R.; Barbour, R.; Berthelette, P.; Blackwell, C.; Carr, T.; Clemens, J.; Donaldson, T.; et al. (Athena Neurosciences, Inc., South San Francisco, Calif., USA), *Alzheimer-type neuropathology in transgenic mice overexpressing V717F β-amyloid precursor protein*, Nature (London) (1995), 373(6514), pp 523-7 (V717F mice);

Neve, R. L.; Boyce, F. M.; McPhie, D. L.; Greenan, J.; Oster-Granite, M. L. (Dep. Genetics, Harvard Medical School and McLean Hospital, Belmont, Mass., USA), *Transgenic mice expressing APP-C100 in the brain*, Neurobiology of Aging (1996), 17(2), pp191-203 (APP-C100 mice);

and/or as disclosed in U.S. Pat. No. 5,811,633; U.S. Pat. No. 5,877,399; U.S. Pat. No. 5,672,805; U.S. Pat. No. 5,720,936; U.S. Pat. No. 5,612,486; U.S. Pat. No. 5,580,003; U.S. Pat. No. 5,850,003; U.S. Pat. No. 5,387,742; U.S. Pat. No. 5,877,015; U.S. Pat. No. 5,811,633; U.S. Pat. No. 6,037,521; U.S. Pat. No. 6,184,435; U.S. Pat. No. 6,187,922; U.S. Pat. No. 6,211,428; and U.S. Pat. No. 6,340,783.

Example 7

Human Testing

Compounds of the present invention may be further tested for their effectiveness in the treatment of disorders mediated by the BACE enzyme, for example Alzheimer's disease, by testing the compounds in human subjects, for example, as disclosed in Lins, H.; Wichart, I.; Bancher, C.; Wallesch, C.-W.; Jellinger, K. A.; Roesler, N. (Department of Neurology, Otto-von-Guericke-University, Magdeburg, Germany), *Immunoreactivities of amyloid β peptide(1-42) and total τ protein in lumbar cerebrospinal fluid of patients with normal pressure hydrocephalus*, Journal of Neural Transmission (2004), 111(3), pp 273-280;

Lewczuk, P.; Esselmann, H.; Otto, M.; Maler, J. M.; Henkel, A. W.; Henkel, M. K.; Eikenberg, O.; Antz, C.; Krause, W.-R.; Reulbach, U.; Kornhuber, J.; Wiltfang, J. (Department of Psychiatry and Psychotherapy, Molecular Neurobiology Lab, University of Erlangen-Nuremberg, Erlangen, Germany), *Neurochemical diagnosis of Alzheimer's dementia by CSF Aβ42, Aβ42/Aβ40 ratio and total tau*, Neurobiology of Aging (2004), 25(3), pp 273-281;

Olsson, A.; Hoglund, K.; Sjogren, M.; Andreasen, N.; Minthon, L.; Lannfelt, L.; Buerger, K.; Moller, H.-J.; Hampel, H.; Davidsson, P.; Blennow, K. (Sahlgrenska University Hospital, Experimental Neuroscience Section, Institute of Clinical Neuroscience, Goteborg University, Moelndal, Sweden), *Measurement of α- and β-secretase cleaved amyloid precursor protein in cerebrospinal fluid from Alzheimer patients*, Experimental Neurology (2003), 183(1), pp 74-80;

Wahlund, L.-O.; Blennow, K. (Karolinska Institute, Section of Geriatric Medicine, Department of Clinical Neuroscience and Family Medicine, Huddinge University Hospital, Stockholm, Sweden), *Cerebrospinal fluid biomarkers for disease stage and intensity in cognitively impaired patients*, Neuroscience Letters (2003), 339(2), pp 99-102;

El Mouedden, M., Vandermeeren, M., Meert, T., Mercken, M. (Johnson & Johnson Pharmaceutical Research and Development, Division of Janssen Pharmaceutica N.V., Turnhoutseweg 30, Beerse, Belg.), *Development of a specific ELISA for the quantitative study of amino-terminally truncated beta-amyloid peptides*, Journal of Neuroscience Methods (2005), 145(1-2), pp 97-105;

Vanderstichele, H., Van Kerschaver, E., Hesse, C., Davidsson, P., Buyse, M.-A., Andreasen, N., Minthon, L., Wallin, A., Blennow, K., Vanmechelen, E., (Innogenetics Nev., Ghent, Belg.), *Standardization of measurement of β-amyloid(1-42) in cerebrospinal fluid and plasma*, Amyloid (2000), 7(4), pp 245-258;

and/or Schoonenboom, N. S., Mulder, C., Van Kamp, G. J., Mehta, S. P., Scheltens, P., Blankenstein, M. A., Mehta, P. D., *Amyloid β38, 40, and 42 species in cerebrospinal fluid: More of the same?*, Annals of Neurology (2005), 58(1), pp 139-142.

Example 8

Oral Formulation—Prophetic Example

As a specific embodiment of an oral composition, 100 mg of the compound prepared as in Example 1 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

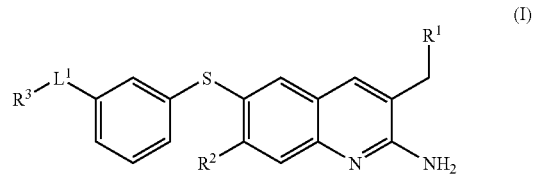

wherein $R^1$ is selected from the group consisting of $C_{1-4}$alkyl, $C_{3-8}$cycloalkyl, 5-6 membered heteroaryl, —($C_{1-4}$alkyl)-(5-6 membered heteroaryl), 5-6 membered heterocycloalkyl and —($C_{1-4}$alkyl)-5-6 membered heterocycloalkyl;

$R^2$ is selected from the group consisting of hydrogen and halogen;

$L^1$ is selected from the group consisting of —$CH_2$—$NR^4$—, —$CH_2CH_2$—$NR^4$—, —$CH_2$—O— and —$CH_2$—S—; wherein $R^4$ is selected from the group consisting of hydrogen, $C_{1-4}$alkyl, —C(O)—$C_{1-4}$alkyl, —C(O)O—$C_{1-4}$alkyl and —$SO_2$—$C_{1-4}$alkyl;

$R^3$ is selected from the group consisting of $C_{1-4}$alkyl, carboxy substituted $C_{1-4}$alkyl, $C_{4-8}$cycloalkyl, —($C_{1-4}$alkyl)-$C_{4-8}$cycloalkyl, partially unsaturated carbocyclyl, —($C_{1-4}$alkyl)-(partially unsaturated carbocyclyl), aryl, —($C_{1-4}$alkyl)-aryl, heteroaryl, —($C_{1-4}$alkyl)-heteroaryl, heterocycloalkyl and —($C_{1-4}$alkyl)-heterocycloalkyl; wherein the $C_{4-8}$cycloalkyl, aryl, heteroaryl or heterocycloalkyl, whether alone or as part of a substituent group is optionally substituted with one or more substituents independently selected from the group consisting of halogen, hydroxy, carboxy, $C_{1-4}$alkyl, fluorinated $C_{1-4}$alkyl, —$C_{1-4}$alkoxy-, fluorinated —$C_{1-4}$alkoxy, —$C_{1-4}$alkyl-OH, —$C_{1-4}$alkyl-$CO_2$H and phenyl;

alternatively, $R^4$ and $R^3$ are taken together with the nitrogen atom to which they are bound to form a ring selected from the group consisting of 5 to 6 membered heteroaryl and 5 to 6 membered heterocycloalkyl;

or a pharmaceutically acceptable salt thereof.

2. A compound as in claim 1, wherein $R^1$ is selected from the group consisting of $C_{3-8}$cycloalkyl, 5-6 membered heteroaryl, —($C_{1-4}$alkyl)-(5-6 membered heteroaryl), 5-6 membered heterocycloalkyl and —($C_{1-4}$alkyl)-5-6 membered heterocycloalkyl;

$R^2$ is selected from the group consisting of hydrogen and halogen;

$L^1$ is selected from the group consisting of —$CH_2$—$NR^4$—, —$CH_2CH_2$—$NR^4$—, —$CH_2$—O— and —$CH_2$—S—; wherein $R^4$ is selected from the group consisting of hydrogen, $C_{1-4}$alkyl and —C(O)O—$C_{1-4}$alkyl;

$R^3$ is selected from the group consisting of $C_{1-4}$alkyl, carboxy substituted $C_{1-4}$alkyl, $C_{4-8}$cycloalkyl, —($C_{1-4}$alkyl)-$C_{4-8}$cycloalkyl, aryl, —($C_{1-4}$alkyl)-aryl, heteroaryl, —($C_{1-4}$alkyl)-heteroaryl, heterocycloalkyl and -($C_{1-4}$alkyl)-heterocycloalkyl; wherein the $C_{4-8}$cycloalkyl, aryl, heteroaryl or heterocycloalkyl, whether alone or as part of a substituent group is optionally substituted with one or more substituents independently selected from the group consisting of halogen, $C_{1-4}$alkyl, fluorinated $C_{1-4}$alkyl, —$C_{1-4}$alkoxy-, fluorinated —$C_{1-4}$alkoxy, —$C_{1-4}$alkyl-OH, —$C_{1-4}$alkyl-$CO_2H$ and phenyl;

alternatively, $R^4$ and $R^3$ are taken together with the nitrogen atom to which they are bound to form a ring selected from the group consisting of 5 to 6 membered heterocycloalkyl;

or a pharmaceutically acceptable salt thereof.

3. A compound as in claim 2, wherein
$R^1$ is selected from the group consisting of 5 to 6 membered heterocycloalkyl;
$R^2$ is selected from the group consisting of hydrogen and halogen;
$L^1$ is selected from the group consisting of —$CH_2$—$NR^4$—, —$CH_2CH_2$—$NR^4$—, —$CH_2$—O— and —$CH_2$—S—; wherein $R^4$ is hydrogen;
$R^3$ is selected from the group consisting of carboxy substituted $C_{1-4}$alkyl, $C_{3-6}$cycloalkyl, aryl, —($C_{1-4}$alkyl)-aryl and —($C_{1-4}$alkyl)-(5 to 6 membered heteroaryl); wherein the $C_{3-6}$cycloalkyl is optionally substituted with phenyl; and wherein the aryl or —($C_{1-4}$alkyl)-aryl is optionally substituted with one to three substituents independently selected from the group consisting of halogen, $C_{1-4}$alkyl, fluorinated $C_{1-4}$alkyl, $C_{1-4}$alkoxy, and —$C_{1-2}$alkyl-$CO_2H$;
alternatively, $L^1$ is —$CH_2$—$NR^4$— and $R^4$ and $R^3$ are taken together with the nitrogen atom to which they are bound to form a 6 membered heterocycloalkyl;
or a pharmaceutically acceptable salt thereof.

4. A compound as in claim 3, wherein
$R^1$ is tetrahydropyranyl;
$R^2$ is selected from the group consisting of hydrogen and fluoro;
$L^1$ is selected from the group consisting of —$CH_2$—NH—, —$CH_2CH_2$—NH—, —$CH_2$—O— and —$CH_2$—S—;
$R^3$ is selected from the group consisting of 1-(1-carboxy-n-butyl), 1S*-(2S*-phenyl)-cyclopropyl, 3-(carboxymethyl)-phenyl, 2-ethoxy-benzyl, 2,4,6-trimethyl-phenyl, 4-trifluoromethyl-benzyl, 2,6-difluoro-benzyl, 2,5-difluoro-benzyl, 2,4-dichloro-benzyl, 2,6-dichloro-benzyl, 2,4-dimethyl-benzyl, 2,5-dimethyl-benzyl, 2,4-dimethoxy-benzyl, 2,4,6-trimethyl-benzyl, 4-imidazolyl-ethyl- and 2-pyridyl-methyl-;
alternatively, $L^1$ is —$CH_2$—$NR^4$— and $R^4$ and $R^3$ are taken together with the nitrogen atom to which they are bound to form 1-piperazinyl;
or a pharmaceutically acceptable salt thereof.

5. A compound as in claim 4, wherein
$R^1$ is tetrahydropyranyl;
$R^2$ is selected from the group consisting of hydrogen and fluoro;
$L^1$ is selected from the group consisting of —$CH_2$—NH—, —$CH_2CH_2$—NH— and —$CH_2$—S—
$R^3$ is selected from the group consisting of 3-(carboxymethyl)-phenyl, 2-ethoxy-benzyl, 4-trifluoromethyl-benzyl, 2,6-difluoro-benzyl, 2,5-difluoro-benzyl, 2,4-dichloro-benzyl, 2,4-dimethyl-benzyl, 2,4-dimethoxy-benzyl and 2,4,6-trimethyl-benzyl;

or a pharmaceutically acceptable salt thereof.

6. A compound as in claim 4, wherein
$R^1$ is tetrahydropyranyl;
$R^2$ is selected from the group consisting of hydrogen and fluoro;
$L^1$ is —$CH_2$—NH—;
$R^3$ is selected from the group consisting of 2-ethoxy-benzyl, 2,6-difluoro-benzyl, 2,5-difluoro-benzyl, 2,4-dichloro-benzyl, 2,4-dimethyl-benzyl and 2,4,6-trimethyl-benzyl;
or a pharmaceutically acceptable salt thereof.

7. A pharmaceutical composition comprising a pharmaceutically acceptable carrier and a compound of claim 1.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A compound selected from the group consisting of a compound of formula (II-a)

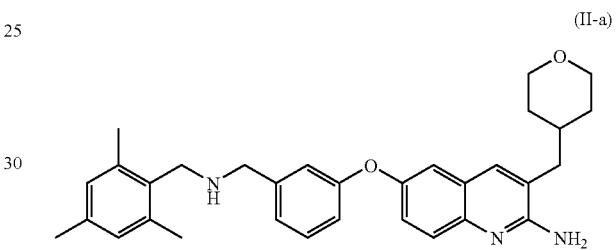

(II-a)

or a pharmaceutically acceptable salt thereof; and a compound of formula (II-b)

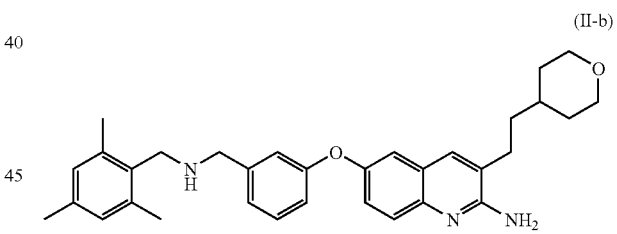

(II-b)

or pharmaceutically acceptable salt thereof.

11. A pharmaceutical composition comprising a pharmaceutically acceptable carrier and a compound of claim 10.

12. A pharmaceutical composition made by mixing a compound of claim 10 and a pharmaceutically acceptable carrier.

13. A process for making a pharmaceutical composition comprising mixing a compound of claim 10 and a pharmaceutically acceptable carrier.

* * * * *